(12) United States Patent
Browning et al.

(10) Patent No.: US 7,162,384 B1
(45) Date of Patent: Jan. 9, 2007

(54) SYSTEM AND METHOD FOR TEMPERATURE COMPENSATION OF EDDY CURRENT SENSOR WAVEFORM PARAMETERS

(75) Inventors: Douglas R. Browning, Denville, NJ (US); Victor G. Mishkevich, Bridgewater, NJ (US); Richard T. Gieske, Newton, NJ (US)

(73) Assignee: General Dynamics Advanced Information, Fairfax, VA (US)

( * ) Notice: Subject to any disclaimer, the term of this patent is extended or adjusted under 35 U.S.C. 154(b) by 0 days.

(21) Appl. No.: 11/230,928

(22) Filed: Sep. 21, 2005

(51) Int. Cl.
G06F 19/00 (2006.01)
(52) U.S. Cl. .......................... 702/99; 374/100
(58) Field of Classification Search ............... 702/99, 702/188, 132
See application file for complete search history.

(56) References Cited

U.S. PATENT DOCUMENTS

| | | |
|---|---|---|
| 3,936,734 A | 2/1976 | Brandli et al. |
| 4,095,469 A | 6/1978 | Yamada et al. |
| 4,173,869 A | 11/1979 | Martin, Jr. et al. |
| 4,408,294 A | 10/1983 | Imdad |
| 4,460,869 A | 7/1984 | Buser et al. |
| 4,468,968 A | 9/1984 | Kee |
| 4,821,204 A | 4/1989 | Huschelrath |
| 4,970,670 A | 11/1990 | Twerdochlib |
| 4,987,555 A | 1/1991 | Twerdochlib |
| 5,140,264 A | 8/1992 | Metala et al. |
| 5,206,816 A | 4/1993 | Hill et al. |
| 5,226,731 A | 7/1993 | Allen |
| 5,258,923 A | 11/1993 | Imam et al. |
| 5,371,462 A | 12/1994 | Hedengren et al. |
| 5,502,999 A | 4/1996 | Seberger et al. |
| 5,596,271 A | 1/1997 | Lowery |
| 5,698,977 A | 12/1997 | Simpson et al. |
| 5,808,202 A | 9/1998 | Passarelli, Jr. |
| 6,094,989 A | 8/2000 | Twerdochlib |
| 6,346,807 B1 | 2/2002 | Slates |
| 6,594,619 B1 | 7/2003 | von Flotow |
| 6,629,463 B1 | 10/2003 | Naudet et al. |
| 6,657,429 B1 | 12/2003 | Goldfine et al. |
| 6,661,222 B1 | 12/2003 | Twerdochlib |
| 6,664,782 B1 | 12/2003 | Slates |
| 6,692,222 B1 | 2/2004 | Prinz et al. |
| 6,785,635 B1 | 8/2004 | von Flotow |
| 2002/0019708 A1 | 2/2002 | Pross |
| 2003/0060986 A1 | 3/2003 | Flotow |
| 2003/0071615 A1 | 4/2003 | Schlicker et al. |
| 2004/0066188 A1 | 4/2004 | Goldfine et al. |
| 2004/0232911 A1* | 11/2004 | Schlicker et al. ........... 324/242 |

* cited by examiner

Primary Examiner—Edward Raymond
(74) Attorney, Agent, or Firm—Steptoe & Johnson LLP

(57) ABSTRACT

An embodiment of the invention generally pertains to a method of compensating for temperature variations in an eddy current sensor signal. The method may include the steps of receiving an initial signal from an eddy current sensor (ECS) in response to a conductive element passing the ECS and sensing an ECS temperature and an ECS board temperature. The method may also include determining a subset of correction coefficients based on the ECS temperature and the ECS board temperature and determining a temperature correction factor from the subset of correction coefficients. The method may then compute a temperature corrected signal from the initial signal and the temperature correction factor.

22 Claims, 5 Drawing Sheets

SYSTEM AND METHOD FOR TEMPERATURE COMPENSATION OF EDDY CURRENT SENSOR WAVEFORM PARAMETERS

GOVERNMENT RIGHTS

The government has certain rights in this invention pursuant to Contract No. N00019-02-C-3003 awarded by the Department of the Navy.

FIELD OF THE INVENTION

This invention relates to eddy current sensors, and particularly to a system and method for compensating an eddy current sensor waveform parameters.

BACKGROUND OF THE INVENTION

Eddy current sensors are known and used in a variety of applications. One use of eddy current sensors is monitoring for defects in turbine blades of a turbine engine. As a turbine blade spins in a turbine engine, the blade is affected by centrifugal forces and vibrations, which may induce material defects in the turbine blade. As material defects grow, the length of the turbine blade may increase and, in some cases, collide with the inner diameter of the turbine casing, causing damage to the turbine engine.

In a typical eddy current application, the eddy current sensor is typically placed within the turbine casing, with the closest distance between the tip of the turbine blade and the eddy current sensor typically referred to as the standoff distance. An output signal from the eddy current sensor is correlated to the standoff distance such that any change in the standoff distance is reflected in a change in the output signal. By comparing multiple measurements of the eddy current signal and the standoff distance, the growth of a turbine blade or other changes in the turbine blade or blade hub may be sensed. By detecting abnormal growth or changes in the turbine blades early, the turbine blades may be replaced or repaired before expensive damage occurs.

FIG. 5 illustrates a conventional eddy current sensor module 500. As shown in FIG. 5, the eddy current sensor module 500 includes an eddy current sensor 510 and an electronic board 520.

The eddy current sensor 510 may be an eddy current sensor such as described in U.S. Pat. No. 5,942,893 (issued Aug. 24, 1999 and common assignee) to Terpay, which is hereby incorporated by reference in its entirety. Alternatively, other eddy current sensors may be obtained from GMW Associates, W. C. Branham, Globalspec or other similar situated vendor. The eddy current sensor 510 is configured to generate a voltage waveform signal as the turbine blade 540 approaches, passes and departs from the eddy current sensor.

Returning to FIG. 5, the voltage signal from the output eddy current sensor 510 may be outputted to the electronic board 520. The electronic board 520 may be configured to supply power to the eddy current sensor 520 with a radio-frequency (RF) amplifier operating, for example, at 15 MHz. The electronic board 520 may also be configured to receive signals from the eddy current sensor 510 and mix the received signal with the frequency of the RF amplifier. The raw analog signal from the mixer is amplified with another amplifier and filtered to generate the eddy current sensor baseband waveform, which is shown in FIG. 6.

FIG. 6 illustrates a baseband waveform 600 from the eddy current sensor 510 for a passing target, e.g., a turbine blade, as processed by the electronic board 520. As shown in FIG. 6, the baseband waveform 600 is plotted on a time versus voltage graph. The baseband waveform 600 includes two peak voltages, $V^+_{peak:T1}$ and $V^-_{peak:T1}$. These two peak values are the largest voltage values, which occur at t+peak and t-peak, respectively. The baseband waveform 600 includes two waveform parameters, the peak-to-peak voltage between $V^+_{peak:T1}$ and $V^-_{peak:T1}$ and the zero crossing slope at time, $t_0$. The slope of the waveform signal at this particular point is characterized by $m_0$. The standoff distance between a conductive element and an eddy current sensor may be determined as an eddy current sensor generated waveform signal as a function of the peak-to-peak voltage waveform parameter.

In constant temperature conditions, the amplitude of $V^+_{peak}$ and $V^-_{peak}$, or the peak-to-peak voltage, increases with a decrease in standoff distance. Unfortunately, the signal produced by the eddy current sensor is impacted by and varies with the temperatures of the eddy current sensor as well as the temperature of the electronics components on the signal conditioning circuit board. Generally, as the temperature rises, the signal diminishes for a fixed standoff distance between the eddy current sensor and the target, as shown in FIG. 6. FIG. 6 includes three waveforms generated at a fixed standoff distance at three different temperatures where T1<T2<T3.

In operation, the eddy current sensors are often exposed to extreme environments like the interior of a turbine engine with varying operating temperatures under different operating and flight conditions. As such, the waveforms generated by the eddy current sensors may not only vary with changes in the actual standoff distance between the eddy current sensors and the turbine blades, but may also vary with the changes in temperature experienced by the eddy current sensor. Additionally, the waveform is also impacted by the temperature of the electronics and wiring used to drive, sense and record the signal generated by the eddy current sensor. Therefore, the recorded eddy current signal may not accurately reflect the true standoff distance because of the impact the temperature of the eddy current sensor and the temperature of the sensor electronics may have on the signal.

Unfortunately, changes in the waveform due to rising changes in the temperature of the sensor and sensor electronics may suggest that the standoff distance is growing, when in fact the standoff distance shrinking. Such data may mislead system operators and maintenance crews into a false sense of security until extensive and costly damage occurs in the aircraft engine. Conversely, lowing changes in the temperature may have the opposite effect, causing maintenance crews to prematurely replace expensive turbine blades, resulting in the waste of healthy turbine blades and the costly waste of money and flying time for the aircraft.

Therefore, there exists a need to compensate for the impact of temperature on the waveform signal and the standoff distance determination so as to improve the accuracy of the collected standoff distance data and the reliability of rotating machinery.

SUMMARY OF THE INVENTION

An embodiment of the invention generally pertains to a method of compensating for temperature variations in an eddy current sensor signal. The method may include the steps of receiving an initial signal from an eddy current sensor (ECS) in response to a conductive element passing the ECS and sensing an ECS temperature and an ECS board temperature. The method may also include determining a subset of correction coefficients based on the ECS temperature and the ECS electronics board temperature and determining a temperature correction factor from the subset of correction coefficients. The method may then compute a temperature corrected signal from the initial signal and the temperature correction factor.

Another aspect of the present invention may include a method of compensating for temperature variations in an eddy current sensor signal. The method may include the steps of generating an initial signal from an eddy current sensor in response to a conductive element passing by the ECS and receiving in a sensor electronics board the initial signal. The method may also include producing a waveform signal from the initial signal, receiving, in a temperature compensation module, the waveform signal from the sensor electronics board, retrieving from the waveform signal a subset of key parameters, and receiving, in the temperature compensation module, an ECS temperature and an sensor electronics board temperature. The method may also include determining a subset of correction coefficients based on the ECS temperature and the sensor electronics board temperature, computing a temperature correction factor from the subset of correction coefficients, computing a subset of temperature corrected key parameters using the temperature correction factor and the subset of subset of key parameters, and determining a standoff distance between the ECS and the conductive element from the subset of temperature corrected key parameters.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures, wherein:

DETAILED DESCRIPTION OF THE PREFERRED EMBODIMENTS

Figure 1:
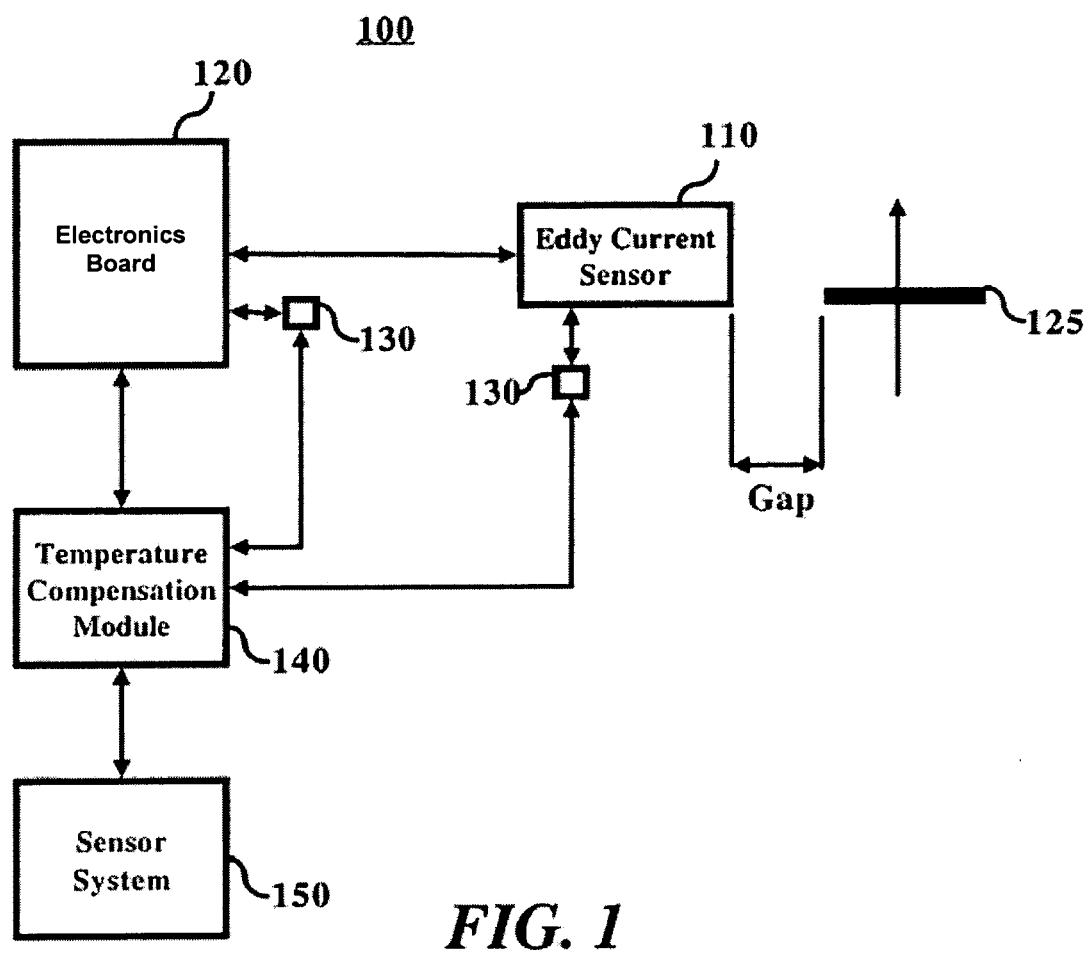
FIG. 1 illustrates a temperature compensation system 100 in accordance with an embodiment of the invention.

For simplicity and illustrative purposes, the principles of the present invention are described by referring mainly to exemplary embodiments thereof. However, one of ordinary skill in the art would readily recognize that the same principles are equally applicable to, and may be implemented in, all types of monitoring systems, and that any such variations do not depart from the true spirit and scope of the present invention. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present invention is defined by the appended claims and their equivalents.

Embodiments of the present invention pertain to a system and method of compensating for temperature in an eddy current sensor (ECS) module. More particularly, a temperature compensation module (TCM) is configured to compensate for the rise and fall of temperatures within the ECS module. The ECS sensor module is typically comprised of the ECS sensor and an electronic board that processes the signals from the ECS sensor. The TCM may also be configured to compute a temperature correction factor or function (TCF) from a subset of correction coefficients or factors associated with the electronic board and ECS sensor at an ambient (or reference) temperature. For example, the subset of correction factors or coefficients may include an RF power amplifier temperature response due to changes in local board temperature while driving a 50 ohm load ($PA1_{TCF}(T_B)$), a power amplifier dependency on sensor temperature whose load impedance varies with temperature ($PA2_{TCF}(T_S)$), a sensor response due to changes in sensor temperature ($S21_{PPTCF}(T_S)$), an RF receiver input impedance temperature effect function ($AINP_{TCF}(T_B, T_S)$), and a temperature sensitivity function for the gain in the electronics signal conditioning path ($Gain_{TCF}(T_B)$). As such, the value of the TCF varies as a function of temperature.

To account for the affect of temperature on the performance of the ECS and the sensor electronics, the TCM is configured to implement a temperature compensation algorithm. To do this, the TCM may receive a signal from the ECS in response to a conductive element passing the ECS. The TCM may also be configured to receive temperature data or determine the temperature of the electronic board ($T_B$) and the temperature of the ECS sensor ($T_S$). The TCM may be further configured to determine the values of the correction factors or correction coefficients, often referred to as key parameters. As discussed below, the determination of the correction coefficients may be accomplished using data structures, such as look-up tables, or best fit curves, such as $2^{nd}$ or $3^{rd}$ order polynomials or other methods known to those of skill in the art. Upon finally computing the TCF using the determined values of the correction factors, the TCF may be applied to the waveform signal or to parameters of the waveform to normalize or standardize each waveform signal to a reference temperature. This may allow different waveforms or standoff distance measurements, taken at different temperatures, to be accurately compared.

FIG. 1 illustrates a temperature compensation system 100 in accordance with an embodiment of the invention. It should be readily apparent to those of ordinary skill in the art that the system depicted in FIG. 1 represents a generalized schematic and that additional components may be added or existing components may be removed or modified.

As shown in FIG. 1, the temperature compensation system 100 includes an eddy current sensor 110, an electronic board 120, temperature sensors 130, and a temperature compensation module 140.

The eddy current sensor 110 and electronic board 120 may be the conventional types as known to those skilled in the art. As discussed previously, the eddy current sensor 110 may be configured to output a voltage signal to the electronic board 120 as the target 125 passes the eddy current sensor. The electronic board 120 may be configured to provide the RF power and timing signals to the eddy current sensor 110. The electronic board 120 may also be configured to process the received signal from the eddy current sensor 120 to a baseband waveform, which may be inputted to the temperature compensation module 140.

In accordance with one embodiment of the present invention, temperature sensor 130 may be configured to monitor the electronic board 120 and a second temperature sensor 130 may be configured to monitor the temperature of the eddy current sensor 110. The outputs of the temperature sensors 130 may be inputted to the temperature compensation module 140. Although temperatures sensors 130 are shown in FIG. 1 in order to sense the temperature of the electronic board 120 and the ECS 110, it should be understood by those of skill in the art that other methods of sensing or determining the temperatures of the electronic board 120 and the ECS 110 may be used without deviating from the scope and spirit of the present invention.

The temperature compensation module 140 may be configured to generate a temperature correction factor (TCF) value based on correction factors or coefficients. Correction factors and coefficients are typically determined off-line by means of controlled tests and simulation prior to application of the TCF to ECS waveform parameters. The correction factors may be dependent on the temperature of the electronic board and the temperature of the sensor. As mentioned, the TCF may be applied to the baseband waveform from the electronic board 120 such that a normalized or standardized waveform signal, at a reference temperature, may be generated. More particularly, the temperature compensation module may be configured to determine a value for the TCF based on the following temperature correction formula as depicted in equation (1):

$$TCF(T_B,T_S) = PA1_{TCF}(T_B)*PA2_{TCF}(T_S)*S21_{PPTCF}(T_S)* AINP_{TCF}(T_B,T_S)*GAIN_{TCF}(T_B) \quad (1)$$

$PA1_{TCF}(TB)$ may be characterized as the RF power amplifier temperature response due to changes in local board temperature while driving a 50 ohm load. In some embodiments, the functional form for $PA1_{TCF}(T_B)$ and the associated coefficients may be determined during initial testing of the temperature compensation system 100. In other embodiments, a look-up table where predetermined values may be returned for a given temperature of the electronic board 120.

$PA2_{TCF}(T_S)$ may be characterized as the power amplifier temperature dependency on sensor temperature whose load impedance value varies with temperature. This formula may in practice be defined using a common functional format (e.g., $2^{nd}$ order polynomial, $3^{rd}$ order rational polynomial) for all power amplifiers, but with different coefficients for each power amplifier that will prescribe an individual power amplifier's temperature dependency. The functional form for $PA2_{TCF}(T_S)$ and coefficients would be determined during initial testing and calibration of the ECS system. In other embodiments, the values for $PA2_{TCF}(T_S)$ are predetermined by testing for given temperature and impedances. The values may then be placed into a look-up table to retrieve values for a given temperature.

$S21_{PPTCF}(T_S)$ may be characterized as the sensor-only temperature sensitivity function. This function may be determined by plotting the performance of the eddy current sensor 110 for a range of temperatures, i.e., empirically. The values may be stored in a data structure, e.g., look-up table, that may be indexed by the temperature of the sensor.

$AINP_{TCF}(T_B, T_S)$ may be characterized as the RF receiver input impedance temperature effect function which is dependant on local board temperature as well as the sensor output impedance whose impedance varies with sensor temperature. This function may be determined empirically by determining the value for various temperatures of the eddy current sensor 110 and the electronic board 120. Subsequently, the values may be placed into a data structure indexed by temperature. $AINP_{TCF}$ includes the impedance transformation by the cables connecting the sensor to the electronics board. Furthermore, laboratory investigation has indicated that the cable impedance has a negligible temperature dependency.

$GAIN_{TCF}(T_B)$ may be characterized as the temperature sensitivity function for the gain in the electronics signal conditioning path. For this function, values may be determined empirically for a range of temperatures.

After computing the $TCF(T_B,T_S)$, the temperature compensation module 140 may be configured to apply the $TCF(T_B,T_S)$ to the waveform signal received from the electronic board 120 or to waveform parameters of the waveform. As shown in equation (2), the waveform parameter of the measured peak-to-peak voltage may be divided by the $TCF(T_B,T_S)$ to compute a standardized or reference peak-to-peak voltage. As such, in accordance with one embodiment of the present invention, temperature compensation of the waveform parameter peak-to-peak voltage may be accomplished by applying the following equation (2):

$$V_{ref_{P-P/SLope}}(Z) = \frac{V_{meas_{P-P/Slope}}(Z, T_B, T_S)}{TCF(T_B, T_S)} \quad (2)$$

Accordingly, the temperature compensation module 140 may adjust or compensate the baseband waveform or a parameter of the waveform for the operating temperatures of the eddy current sensor and the electronic board 120. As shown in equation (2), the measured peak-to-peak voltage, recorded at a temperature of TB and TS, may be normalized to a peak-to-peak voltage at a reference temperature where the impact of the temperature on the waveform parameter is substantially eliminated. This corrected parameter or waveform may be forwarded to the sensor system 150 to be analyzed further. In particular, the standoff distance between the eddy current sensor and the conductive element may be determined from the corrected waveform parameter or corrected waveform. In other embodiments, the corrected value may be stored in persistent storage for later analysis. By improving the accuracy of the output signal from the eddy current sensor 110, which is passed through the electronic board 120, the accuracy of the standoff determination may be significantly improved. As such, the costly replacement or maintenance of rotating machinery, such as jet engines, may be more efficiently managed. Further, the prediction of engine failure or damage may be made more precise by analyzing more accurate standoff distance measurements, helping to improve the reliability of jet engines and the like.

It should be understood that the temperature compensation and standoff distance determination may be accomplished in real time such that system controllers or pilots may make real time decisions about the health and capabilities of an aircraft engine or other rotating machine. However, it should also be clear to those of skill in the art that the waveform signal received from the electronic board 120 and the sensed temperature of the eddy current sensor 110 and the electronic board 120, at the time the waveform signal is received, may be simply recorded. For example, flight data regarding the health of an aircraft engine may be simply recorded during flight such that temperature corrected standoff distances may be calculated after the flight has landed.

It should also be understood that the electronic board 120, the TCM 140, and the sensor system 150 may be combined into a single set of hardware and software without deviating form the scope and spirit of the present invention. Likewise, other combinations of functions and locations may be possible for the electronic board 120, the TCM 140, and the sensor system 150.

Figure 2:
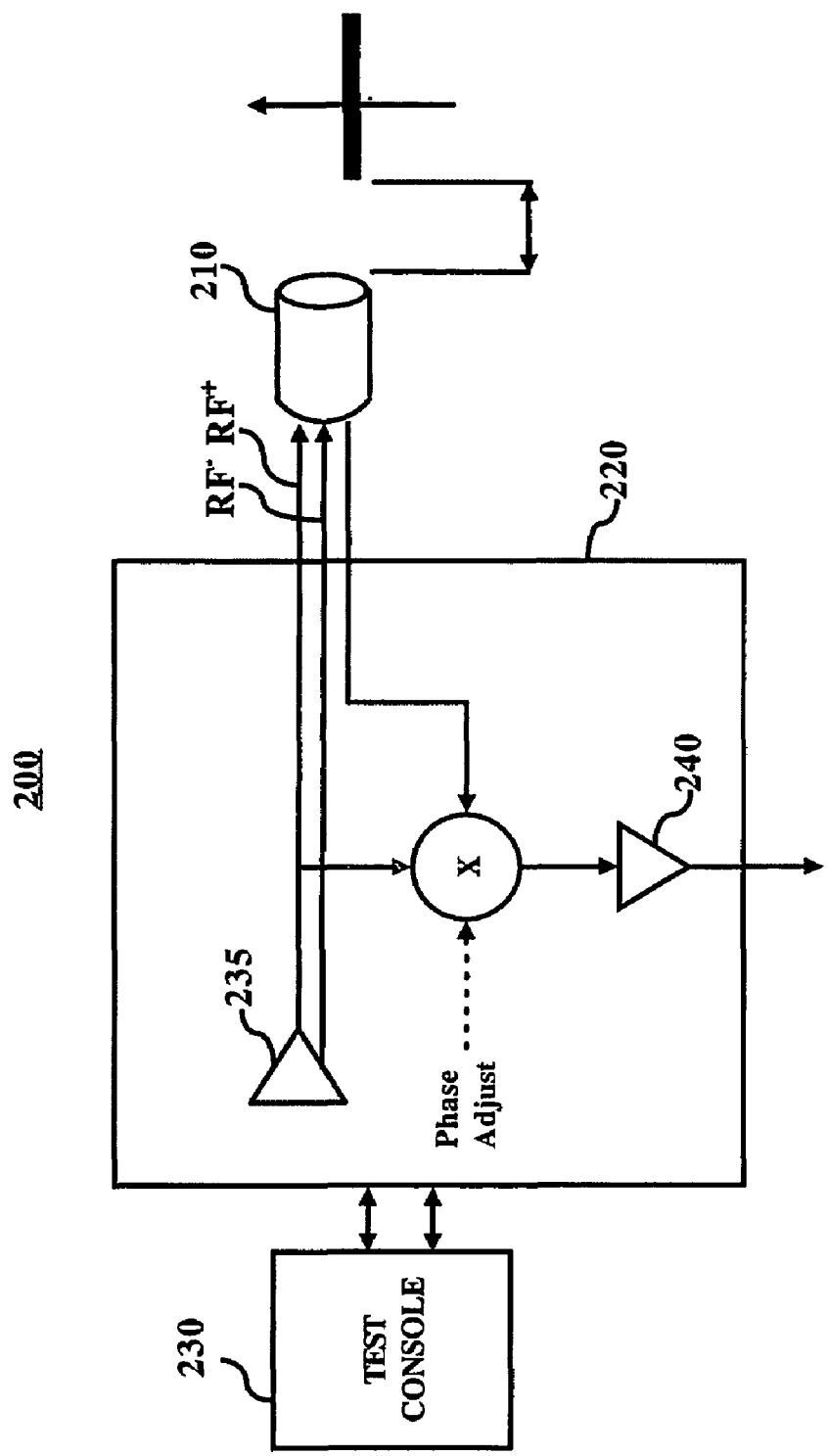
FIG. 2 illustrates a reference testing system in accordance with another embodiment of the invention.

FIG. 2 illustrates a test environment 200 to determine the key parameters for the temperature correction factor in accordance with an embodiment of the invention. It should be readily apparent to those of ordinary skill in the art that the system depicted in FIG. 2 represents a generalized schematic and that additional components may be added or existing components may be removed or modified.

As shown in FIG. 2, the test environment 200 includes an eddy current sensor 210, an electronic board 220 and a test console 230. The eddy current sensor 210 and the electronic board 220 may be implemented with conventional devices known to those skilled in the art. The test console 230 may be device that is programmed to determine the value of the key parameters for a range of temperatures and/or conditions.

The electronic board 220 includes a radio frequency (RF) amplifier 235 operating at 15 MHz. The RF amplifier 235 may be configured to power the eddy current sensor 210 with a RF$^+$ and RF$^-$ drive signals. In some embodiments, an impedance matching circuit may be placed along the path of the RF$^+$ and RF$^-$ signals to match the impedance of the eddy current sensor 210. The RF amplifier 235 may also have its performance affected by temperature. Therefore, $PA1_{TCF}(T_B)$ is used as one of the temperature correction functions to account for performance of the RF amplifier 235. The test console 230 may be used to generate values for a range of temperatures.

The electronic board 220 also includes a second power amplifier 240 that provides for baseband waveform gain and filtering. The power amplifier 240 may also have its performance affected by temperature. Therefore, $PA2_{TCF}(T_S)$ is used as one of the temperature correction functions to account for the temperature dependent performance of power amplifier 240.

The electronic board 220 also includes a mixer 245 which receives a signal from the eddy current sensor as well as the RF$^+$ signal. The mixer 245 may function as an RF receiver. The performance of the mixer 245 is also affected by temperature. More specifically, the input impedance is dependant on the local board temperature as well as the sensor output impedance which varies with the sensor temperature. The performance of the mixer 245 can be characterized by the key parameter $AINP_{TCF}(T_B, T_S)$. The test console can determine values for a given range of temperatures for $T_B$ and $T_S$.

The strength of the signal from the eddy current 210 is amplified by the signal processing components of the electronic board 220. The gain associated with the signal processing is also temperature dependant and can be characterized by the key parameter $GAIN_{TCF}(T_B)$. The test console 230 can be used to determine values of $GAIN_{TCF}(T_B)$ for a given range of temperatures.

Although not associated with the electronic board 220, the performance of the eddy current sensor 210 is also affected by temperature. The temperature-dependant performance of the eddy current sensor 210 can be characterized by the function $S21_{PPTCF}(T_S)$. The test console 230 can be used to determine values of $S21_{PPTCF}(T_S)$ for a selected range of temperatures.

Figure 3:
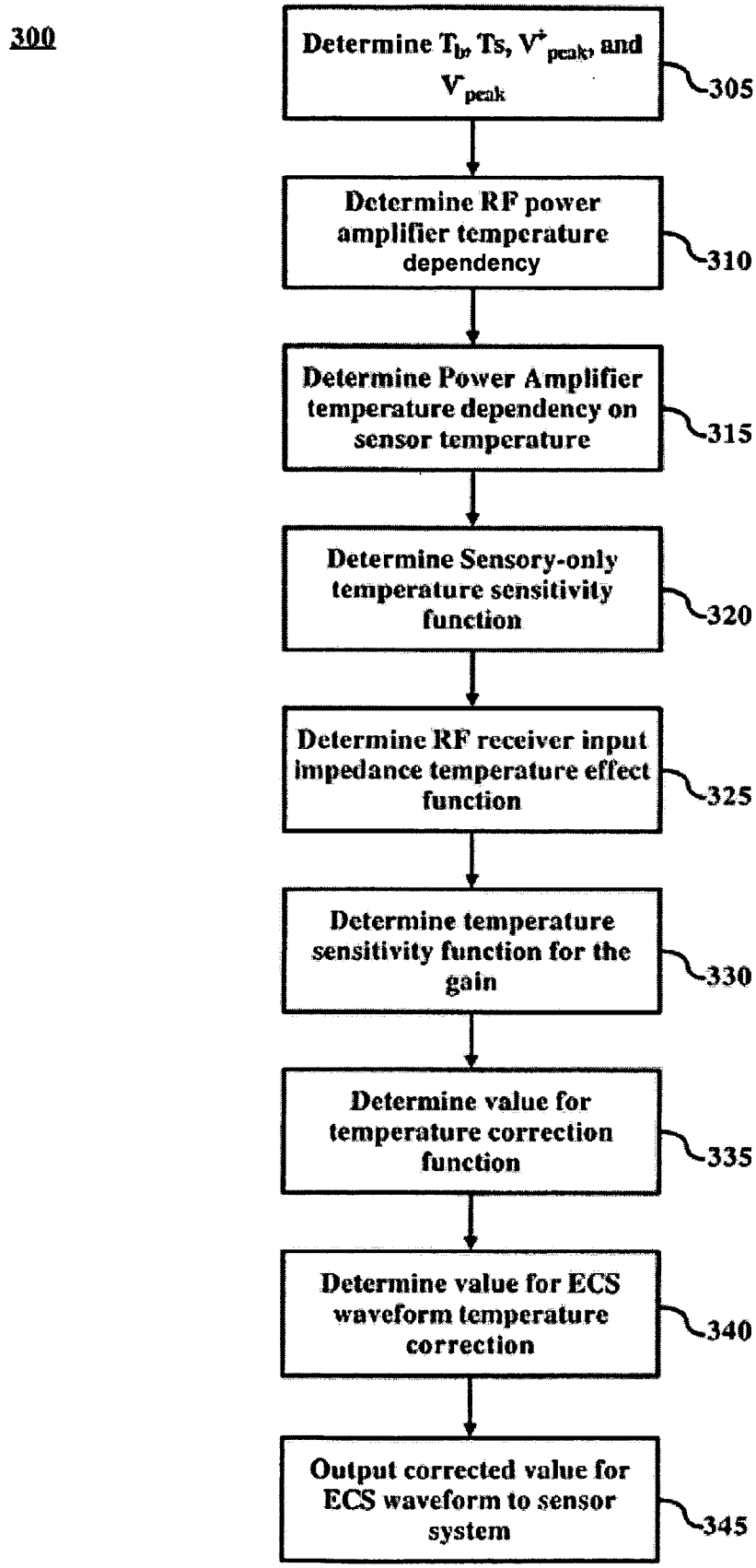
FIG. 3 illustrates a flow diagram for the operation of a temperature compensation module in accordance with yet another embodiment.

FIG. 3 illustrates a flow diagram 300 in accordance with an embodiment of the invention. It should be readily apparent to those of ordinary skill in the art that the flow diagram 300 depicted in FIG. 3 represents a generalized method and that additional steps may be added or existing steps may be removed or modified.

As shown in FIG. 3, the temperature compensation module 140 may be configured to receive $V_{meas}$ as from the electronic board 120, in step 305. More particularly, the temperature compensation module 140 may receive the baseband signal as processed by the electronic board 120 from the eddy current sensor 110. The baseband signal, $V_{meas}$ may include value of voltage peaks, positive (V$^+$) and negative (V$^-$), and the slope at the zero crossing point. The temperature compensation module 140 may also receive the sensed temperature from the temperature sensors 130 for the eddy current sensor 110 and the electronic board 120.

In step 310, the temperature compensation module 140 may be configured to determine $PA1_{TCF}$ for the given $T_B$. In one embodiment, the temperature compensation module 140 may have a look-up table that stores corresponding values of $PA1_{TCF}$ for a range of $T_B$, where the look-up table is indexed by the electronic board temperature. Accordingly, the temperature compensation module 140 may search the look-up table for the corresponding value of $PA1_{TCF}$ for the sensed temperature, TB.

In step 315, the temperature compensation module 140 may determine $PA2_{TCF}$ for the sensed temperature of the eddy current sensor, $T_S$. In another embodiment, the temperature compensation module 140 may use a data structure to retrieve the value for $PA2_{TCF}$ for the particular $T_S$.

In step 320, the temperature compensation module 140 may determine $S21_{PPTCF}$ for the sensed temperature of the eddy current sensor, $T_S$. In one embodiment, the temperature compensation module 140 may retrieve the value for $S21_{PPTCF}$ by searching a data structure with $T_S$.

In step 325, the temperature compensation module 140 may determine $AINP_{TCF}$ for the sensed board temperature, $T_B$, and eddy current sensor 110, $T_S$. In yet another embodiment, the temperature compensation module 140 may retrieve the value for $AINP_{TCF}$ by searching a data structure with $T_S$ and $T_B$.

In step 330, the temperature compensation module 140 may determine the $GAIN_{TCF}$ for the temperature of the electronic board 120, $T_B$. In some embodiments, the temperature compensation module 140 may retrieve the value for $GAIN_{TCF}$ by searching a data structure with $T_B$.

In step 335, the temperature compensation module 140 may be configured to determine the value for the temperature correction factor as previously discussed with respect to equation 1. More particularly, the temperature compensation module 140 may take the values of the determined key parameters or correction coefficients and take the dot product according to equation 1 to arrive at the value of the temperature correction factor.

In step 340, the temperature compensation module 140 may be configured to apply the value of the temperature correction factor to the baseband waveform according to equation 2. The temperature corrected baseband waveform is then forwarded to the sensor system 150 in step 345. It should also be understood that the temperature correction factor may be applied to waveform parameters extracted from the waveform signal received from the electronic board 120, such at the peak-to-peak voltage or zero crossing slope.

The standoff distance between the eddy current sensor and the conductive element may be determined from the temperature corrected waveform signal or temperature corrected waveform pattern as a manner know to those of skill in the art.

Figure 4:
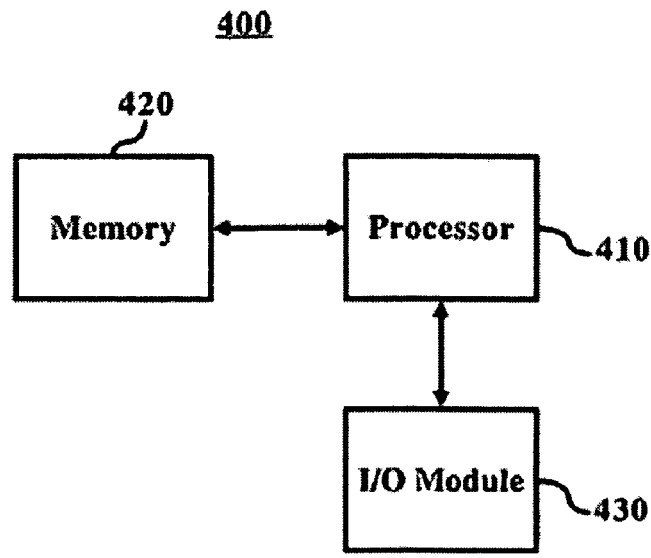
FIG. 4 illustrates a computing platform in accordance with yet another embodiment.
Figure 5:
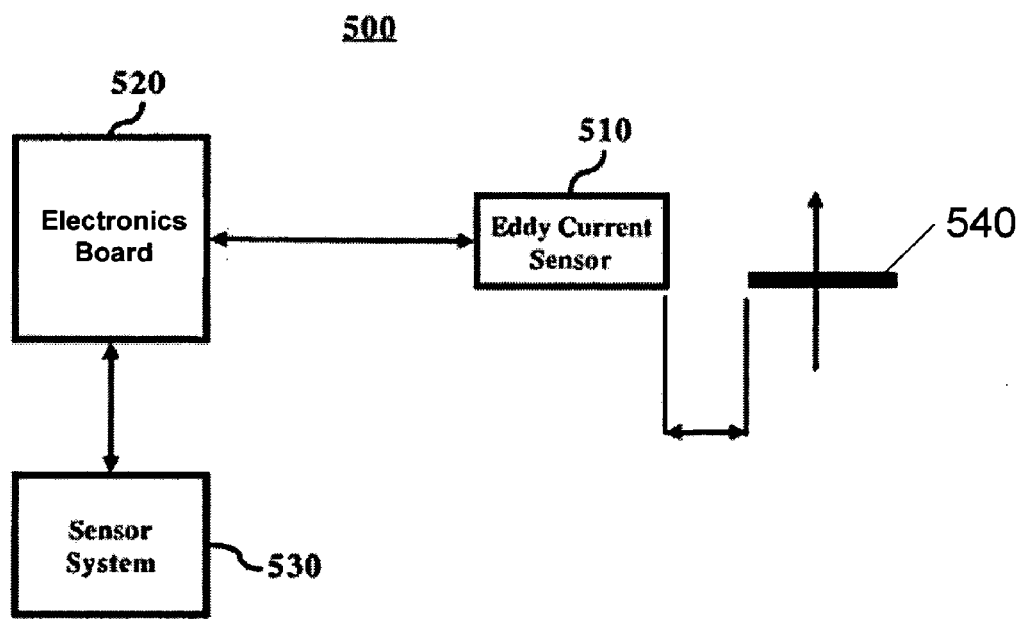
FIG. 5 illustrates a conventional eddy current sensor with electronic board.
Figure 6:
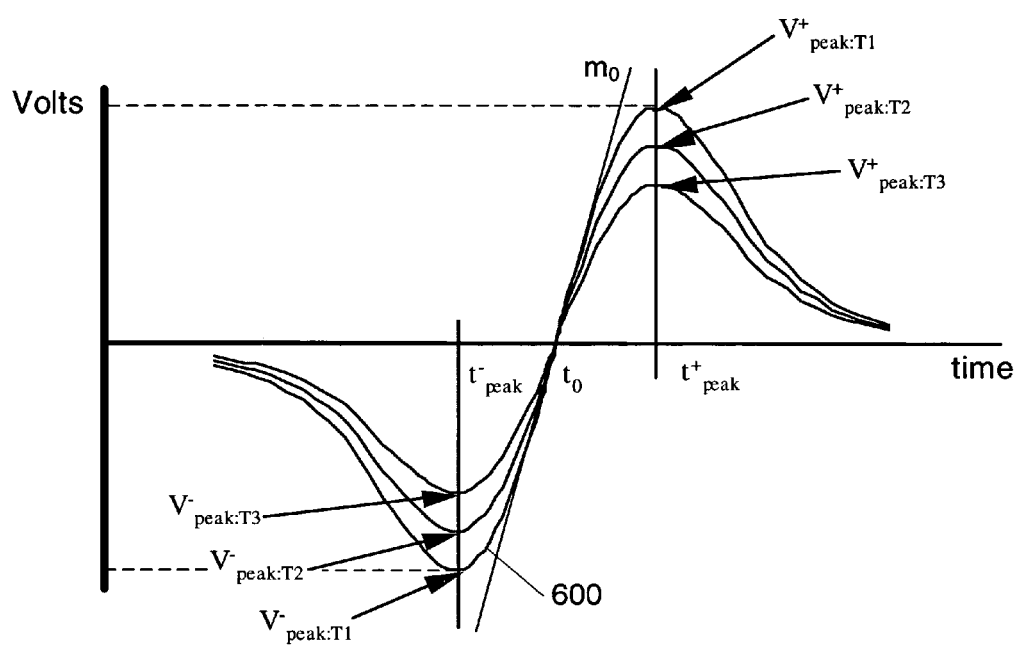
FIG. 6 illustrates a baseband waveform as processed by the electronic board.

FIG. 4 illustrates a computing platform 400 that may implement the temperature compensation module 140 in accordance with another embodiment of the invention. It should be readily apparent to those skilled in the art that FIG. 4 illustrates a generalized schematic and additional components may be added or existing components removed and/or modified.

As shown in FIG. 4, the computing platform 400 includes a processor 410, memory 420, and input/output (I/O) module 430. The processor 410 may be implement with a microprocessor, digital signal processor, application specific integrated circuit or other similar device. The processor 410 may be configured to implement the software that represents the functionality of the temperature compensation module 140.

The processor 410 may be interfaced with memory 420. The memory 420 may be persistent, non-persistent or some combination thereof. The memory 420 may be configured to store the software that implements the functionality of the temperature compensation module 140. The memory 420 may also be configured to serve as storage area as needed for computational analysis. The memory 420 may also store data structures related to the computations such as look-up tables and/or other data.

The processor 410 may also be interfaced with an I/O module 430. The I/O module 430 may be configured to receive the baseband waveform from the electronic board 120 as well as to output the corrected baseband waveform.

Certain embodiments may be performed as a computer program. The computer program may exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present invention can be configured to access, including signals downloaded through the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

The invention claimed is:

1. A method of compensating for temperature variations in an eddy current sensor signal, the method comprising the steps of:
   receiving an initial signal from an eddy current sensor (ECS) in response to a conductive element passing the ECS;
   sensing an ECS temperature and an ECS board temperature;
   retrieving values for a subset of correction coefficients based on at least one of the ECS temperature and the ECS board temperature;
   computing a temperature correction factor from the values for the subset of correction coefficients; and
   applying the temperature correction factor to the initial signal.

2. The method according to claim 1, further comprising the step of identifying a waveform parameter in the initial signal.

3. The method according to claim 2, wherein the waveform parameter includes at least one of the peak-to-peak voltage and zero crossing slope.

4. The method according to claim 3, wherein the step of applying the temperature correction factor includes computing a normalized waveform parameter by applying the temperature correction factor to the waveform parameter.

5. The method according to claim 4, wherein the normalized waveform parameter includes at least one of a normalized peak-to-peak voltage and a normalized zero crossing slope.

6. The method according to claim 4, further comprising the step of retrieving a standoff distance corresponding to the normalized waveform parameter, the standoff distance being a distance between the ECS and the conductive element.

7. The method according to claim 4, further comprising the step of computing a standoff distance from the normalized waveform parameter, the standoff distance being a distance between the ECS and the conductive element.

8. The method according to claim 1, wherein the subset of correction coefficients includes at least one of a RF power amplifier temperature dependency on the ECS board temperature, a power amplifier dependency on the ECS temperature, an ECS dependency on the ECS temperature, an RF receiver input impedance dependency on the ECS temperature and the ECS board temperature, and an electronics signal gain dependency on the ECS board temperature.

9. The method according to claim 8, wherein the step of retrieving the values for the subset of correction coefficients includes retrieving the values in data structures.

10. The method according to claim 8, wherein the step of retrieving the values includes computing the values for the subset of correction coefficients with at least one of a $2^{nd}$ order polynomial and a $3^{rd}$ order polynomial.

11. The method according to claim 9 or 10, wherein the step of applying the temperature correction factor includes generating a normalized waveform signal.

12. The method according to claim 1, further comprising the step of identifying a waveform parameter in the normalized waveform signal.

13. The method according to claim 12, wherein the waveform parameter include at least one of the peak-to-peak voltage and zero crossing slope.

14. The method according to claim 12, further comprising the step of retrieving a standoff distance corresponding to the waveform parameter, the standoff distance being a distance between the ECS and the conductive element.

15. The method according to claim 12, further comprising the step of computing a standoff distance from the waveform parameter, the standoff distance being a distance between the ECS and the conductive element.

16. The method according to claim 12, wherein the conductive element is a turbine blade.

17. A method of compensating for temperature variations in an eddy current sensor signal, the method comprising the steps of:
generating an initial signal from an eddy current sensor (ECS) in response to a conductive element passing by the ECS;
receiving in a sensor electronics board the initial signal;
producing a waveform signal from the initial signal;
receiving, in a temperature compensation module, the waveform signal from the sensor electronics board;
receiving, in the temperature compensation module, an ECS temperature and an sensor electronics board temperature;
retrieving values for a subset of correction coefficients, each value being based on at least one of the ECS temperature and the sensor electronics board temperature;
computing a temperature correction factor from the values for the subset of correction coefficients;
determining from the waveform signal a waveform parameter;
computing a normalized waveform parameter from the temperature correction factor and the waveform parameter; and
determining a standoff distance from the normalized waveform parameter, the standoff distance being a distance between the ECS and the conductive element.

18. The method according to claim 17, wherein the waveform parameter includes at least one of a peak-to-peak voltage and a zero crossing slope.

19. The method according to claim 17, wherein the subset of correction coefficients includes at least one of a RF power amplifier temperature dependency on the ECS board temperature, a power amplifier dependency on the ECS temperature, an ECS dependency on the ECS temperature, an RF receiver input impedance dependency on the ECS temperature and the ECS board temperature, and an electronics signal gain dependency on the ECS board temperature.

20. The method according to claim 19, wherein the step of retrieving the values for the subset of correction coefficients includes retrieving the values in data structures.

21. The method according to claim 19, wherein the step of retrieving the values includes computing the values for the subset of correction coefficients with at least one of a $2^{nd}$ order polynomial and a $3^{rd}$ order polynomial.

22. The method according to claim 17, wherein the conductive element is a turbine blade.

* * * * *